(12) United States Patent
Hugo et al.

(10) Patent No.: US 6,186,789 B1
(45) Date of Patent: *Feb. 13, 2001

(54) DENTAL TOOL FOR PREPARING A TOOTH FOR A DENTAL CROWN

(75) Inventors: Burkhard Hugo, Hettstadt; Walter Mössle, Mittelbiberach, both of (DE)

(73) Assignee: Kaltenbach & Voigt GmbH, Biberach (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/129,084

(22) Filed: Aug. 5, 1998

(30) Foreign Application Priority Data

Aug. 20, 1997 (DE) ............................................. 197 36 238

(51) Int. Cl.[7] ........................................................ A61C 3/06
(52) U.S. Cl. .......................... 433/166; 433/119; 433/218
(58) Field of Search ...................... 433/118, 119, 433/166, 218, 75, 165

(56) References Cited

U.S. PATENT DOCUMENTS

| | | | |
|---|---|---|---|
| 1,480,730 | * 1/1924 | Lentz | 433/165 |
| 2,924,013 | 2/1960 | Wowra | 433/116 |
| 2,990,616 | * 7/1961 | Balamuth et al. | 433/119 |
| 3,133,351 | 5/1964 | Von Seggern | 433/119 |
| 3,241,239 | * 3/1966 | Ellis | 433/166 |
| 3,924,335 | 12/1975 | Balamuth et al. | 433/119 |
| 4,353,696 | * 10/1982 | Bridges | 433/166 |
| 4,526,541 | 7/1985 | Hubschmid | 433/165 |
| 4,666,405 | 5/1987 | Ericson | 433/229 |
| 4,696,646 | 9/1987 | Maitland | 433/149 |
| 4,726,770 | 2/1988 | Kurer | 433/229 |
| 4,731,019 | * 3/1988 | Martin | 433/166 |
| 4,971,558 | 11/1990 | Jacobi | 433/226 |
| 4,993,951 | 2/1991 | Schumacher | 433/226 |
| 5,098,300 | 3/1992 | Zaki | 433/229 |
| 5,489,208 | 2/1996 | Mandell | 433/165 |
| 5,505,617 | 4/1996 | Skeppmark et al. | 433/118 |
| 5,531,722 | 7/1996 | Van Hale | 604/280 |
| 5,567,156 | 10/1996 | Hagne et al. | 433/226 |
| 6,022,217 | 2/2000 | Hugo | 433/166 |

FOREIGN PATENT DOCUMENTS

| | | |
|---|---|---|
| 3404550A1 | 8/1985 | (DE) . |
| 29609344 U1 | 9/1996 | (DE) . |
| 29620686 U1 | 4/1997 | (DE) . |
| 19736236 | 7/1998 | (DE) . |
| 0646435 | 8/1985 | (EP) . |
| WO96/14024 | 5/1996 | (WO) . |

* cited by examiner

Primary Examiner—John J. Wilson
(74) Attorney, Agent, or Firm—Fitzpatrick, Cella, Harper & Scinto (57) ABSTRACT

A dental tool having a processing section at one end which includes a longitudinally extending lateral face and a transversely extending front face having an abrasive working face located at a distance from the lateral face so as to permit forming a precise marginal edge around a tooth to permit precise positioning of a crown while avoiding deleterious working of the tooth region nearest the stump on which the crown is to be mounted.

11 Claims, 4 Drawing Sheets

DENTAL TOOL FOR PREPARING A TOOTH FOR A DENTAL CROWN

BACKGROUND OF THE INVENTION

1. Technical Field

The invention relates to a dental tool for preparing a tooth for a dental crown.

2. Background Information

Various tools are available for the preparation of a tooth by machining, the effectiveness of such tools being based on differing functional methods. Files having elongated and flat processing bodies have become known that have an abrasive working face on one broad side and, given an oscillating movement with amplitudes directed in the longitudinal direction of the file, are suitable for surface processing of the tooth. The magnitude of the amplitudes of movement is considerable and generally amounts to several millimeters. A cavity in the tooth cannot be worked with such a file. This applies in particular to a cavity having a basal surface transverse to the direction of working. With respect to such a basal surface the file is not only ineffective but the basal surface interferes with the movement of the file, so that damage to the file and breakage thereof would occur if it were to be used for the preparation of such a cavity.

In WO 96/14024 a tool is described having an abrasive processing section which is effective laterally and frontally and which is suitable, with an oscillating drive in the sense of a vibration which is transmitted to the tool by a dental handpiece, for preparing a lateral cavity in a tooth. With this known design the processing section is a processing head which is thickened with respect to the tool shank and which has a cross-sectional shape converging towards its free end. On the side located opposite the lateral processing section the tool has a smooth face. As a result, the known tool is suitable for working a cavity in the approximal region of a tooth. In the course of this working procedure the processing section is preferably lowered from the occlusal region towards the cervical region. In this connection the cavity may have already been worked beforehand by means of a rotary tool or it may also be prepared with the processing section without preliminary work. In the process the adjacent tooth remains unimpaired, since the smooth face located opposite the processing section does not damage the adjacent tooth.

The abrasiveness of the effective working faces of the processing section is created by means of a studding of juxtaposed small grains of hard material, preferably of diamond. In functional operation the small hard grains prove to be a plurality of cutting edges, the working faces that are present in each case being effective over substantially their entire area.

The amplitudes of the oscillating movements of the processing section in functional operation may be executed by three-dimensional, circular or elliptical movements in the sense of a vibration. In order to avoid jamming in the course of extracting the tool from the cavity, the processing section has a cross-sectional shape that is convergent towards its free end.

With this known design the tool has the working face on its side facing the tooth, on its long sides extending transverse thereto and on its front side, said working face extending continuously in the region of these sides.

Since, on account of the short-stroke vibrational drive with an existing tool, on the one hand the preparatory capacity is comparatively low and on the other hand in the case of a crown preparation a relatively large amount of tooth substance has to be worked out, it is advantageous to prepare a crown preparation with a conventional rotating tool in such a way that a tooth stump is formed having a lateral free space which is filled out with the crown to be mounted on top.

It is moreover known that the edge region between the circumferential surface of a tooth and the face pertaining to the marginal region of the crown preparation that runs into the circumferential surface is sensitive and has a tendency to break off. This is to be ascribed to the fact that the dental enamel has a prismatic structure, the prisms being bounded by imaginary radial lines emanating from the centre of the tooth. In this connection the tooth may be imagined as a truncated egg or a truncated cone which is arranged in the gum in countersunk manner. With a view to preventing the dental enamel from breaking off in the region of the edge described above, it has already been proposed to break the edge through the provision of a chamfer and to fill out this chamfer with a marginal web disposed on the free margin of the crown in such a way that the free lateral face of the tooth and the free lateral face of the crown pass into one another in stepless manner.

SUMMARY OF THE INVENTION

The object underlying the invention is to design a tool of the type specified in the introduction in such a way that a crown preparation conforming to requirements can be obtained in simple manner.

This object is achieved by virtue of a dental tool for preparing a tooth for a dental crown, consisting of an elongated tool shank which at one end is connected to a processing section having an abrasive working face extending along and/or transverse to the centre axis of the tool shank and which has a functional region extending over lateral face and the front face of the processing section located opposite the tool shank, the lateral face being smooth on a longitudinal section or overall and/or the front face being smooth on a transverse section or overall.

The tool according to the invention is preferably equipped for secondary preparation of a preliminary preparation produced beforehand by a preferably rotating tool. In this connection the lateral face and/or the front face comprises at least one surface section that is smooth. In both cases the tool consequently comprises a guide face which is constituted by the smooth face and which enables its guidance by abutment either against the lateral face of the tooth stump produced beforehand or against the stepped face of the free space. As a result, it is possible for preparatory work in respect of the tooth to be performed in simple manner so as to conform to requirements, so that an efficient preparation is obtained having a well-fitting shape. This favours the renovation of the tooth, since the useful life of a crown is dependent on a well-fitting shape of the preparation.

It is advantageous to embed the abrasive or erosive working-face region of the tool into the surface of the processing section, preferably to arrange it in a depression in such a way that the working face passes in stepless manner into the surface region that is adjacent in each case.

An advantageous embodiment of the invention consists in that a guide face is present both laterally and frontally, so that two guide faces transverse to one another are predefined on which the tool is guided in stable manner.

The free space in respect of a tooth preparation for a crown is adapted as extensively as possible to the marginal contour of the gum. This results in a curved contour of the stepped face bounding the free space, said stepped face being in most cases concave in the lateral region and convex in the approximal region.

The object further underlying the invention is to design an existing tool in such a way that an adaptation of the free space pertaining to the tooth receiving the crown to the contour of the gum is possible.

This object is achieved by virtue of a dental tool for preparing a tooth for a dental crown, consisting of an elongated tool shank which at one end is connected to a processing section having an abrasive working face extending along and/or transverse to the centre axis of the tool shank and which has a functional region extending over a lateral face and the front face of the processing section located opposite the tool shank, the front face being shaped in convex manner in the direction of view transverse to the lateral face.

With this design according to the invention the free front face of the tool transverse to the lateral face that is turned towards the tooth is formed in convex manner. As a result, the tool is suitable to prepare both a concave and a convex contour of the stepped face that bounds the free space of the crown.

If an existing tool is prevented from executing its oscillating movement there is a risk that it may be overloaded and damaged by reason of resultant impulse effects and may break off, particularly when the tool is simultaneously subject to lateral loads.

Preferably the dental tool comprises in the region of its tool shank a damping means which is effective in the axial direction and/or lateral direction. Preferably, the damping means is arranged in the transitional region between the tool shank and the processing section. Preferably, the tool shank is constituted by an intermediate member made of elastically deformable material, in particular plastic or rubber. Preferably, the damping means is integrated into the rotary joint.

The object further underlying the invention is to avoid or at least reduce the risk of such damage to the tool.

This object is achieved by virtue of a dental tool for preparing a tooth for a dental crown, consisting of an elongated tool shank which at one end is connected to a processing section having an abrasive working face extending along and/or transverse to the centre axis of the tool shank, characterised in that it comprises in the region of its tool shank a damping means which is effective in the axial and/or lateral direction.

With this design the tool comprises a damping means disposed above its processing section which damps the loading of the tool and therefore protects the tool. The damping means transmits the motive force substantially unchanged, but the force is transmitted in yielding manner, so that when the tool is prevented from executing its oscillating movement the motive-force and loading peaks are attenuated. The damping element may be effective radially and/or axially.

With the tool according to the invention and the handpiece according to the invention it is possible both for partial crowns that extend only over a peripheral section of the tooth and for full crowns to be advantageously prepared and fitted. In both cases a rotation of the tool about the longitudinal axis thereof is required during the feed movement in the peripheral direction of the tooth, so that the functional region of the processing section is always turned towards the tooth. In order to achieve this, several designs according to the invention are proposed.

On the one hand this can be achieved by the tool consisting of two parts arranged in series in its longitudinal direction which are connected to one another so as to be freely rotatable in a rotary bearing or rotary joint. On the other hand the tool may be rotatably supported in the handpiece. These designs enable continuous adaptation of the processing section to the particular angular position of the tooth, without the person performing the treatment having to adjust a different rotary position of the tool with respect to the handpiece.

In order to be able to leave the processing section of the tool in a particular rotary position for a definite purpose during the abrasive processing it is advantageous to arrange a locking device in the region of the rotary bearing or rotary joint described above, with which the free rotary capacity of the processing section is capable of being blocked so that the latter remains in its particular rotary position. In this connection it is advantageous to construct the locking device in such a way that it comes into operation automatically whenever the processing section is shifted laterally and/or axially under the loading force arising during the preparation.

The locking device is particularly suitable in conjunction with a swivel joint that enables an oscillating lateral movement of the tool contrary to lateral elastic restoring forces, so that it is centred by the restoring forces. With such a design it is possible for the locking device to be automatically switched on and switched off again as a result of the evasive movement of the processing section under the loading force. The swivelling capacity of the tool or processing section, supported in oscillating manner, contrary to a restoring force centring it enables, on the one hand, an evasive movement of the processing section and, on the other hand, a swivelling or tilting of the handpiece during processing.

The invention and further advantages that can be achieved with it are elucidated in more detail below on the basis of advantageous designs and drawings.

DESCRIPTION OF THE PREFERRED EMBODIMENTS

The tool generally designated by 1 has an elongated structural shape and consists of a rod-shaped tool shank 2 and a processing section 3 which adjoins one end of said tool shank and is thickened at least in a cross-sectional dimension in the form of a head, as a result of which a front broad side 4a, a rear broad side 4b and two narrow sides 4c, 4d extending transverse thereto are present which extend substantially along the centre axis 5 of the tool 1.

The lateral face of the processing section 3 disposed on the front broad side 4a is a broad lateral face 7, extending upwards in substantially straight manner and optionally flat, which extends parallel to the centre axis of the tool shank 2 or of the processing section 3 or may include with said centre axis an acute angle W of about 3 to 80, in particular about 5°, which is closed towards the free front end. In this connection the broad lateral face 7 and the associated circumferential surface of the tool shank 2 may pass into one another at an obtuse angle, or the broad lateral face 7 may be offset laterally outwards, so that a stepped face 8 is present in between. The narrow-side lateral faces 4c, 4d extend substantially parallel to the centre axis 5, whereby in the transverse direction they may likewise be arranged parallel to one another or may include an acute angle W1 which may amount to about 10 to 200 and is open in the radially outward direction.

On the front face 6 the processing section 3 comprises a first front-face section 9 which extends transverse to the centre axis 5, preferably passes in rounded manner into the broad lateral face 7 and includes with the centre axis 5 an angle W2 of about 90° to 100°, preferably a slightly obtuse angle of about 95° which is open towards the tool shank 2.

The front-face section 9 is adjoined laterally by a chamfered processing face 11 which includes with the centre axis 5 an obtuse angle W3 that is greater than the angle W2 and amounts to about 120° to 135°.

Figure 1:
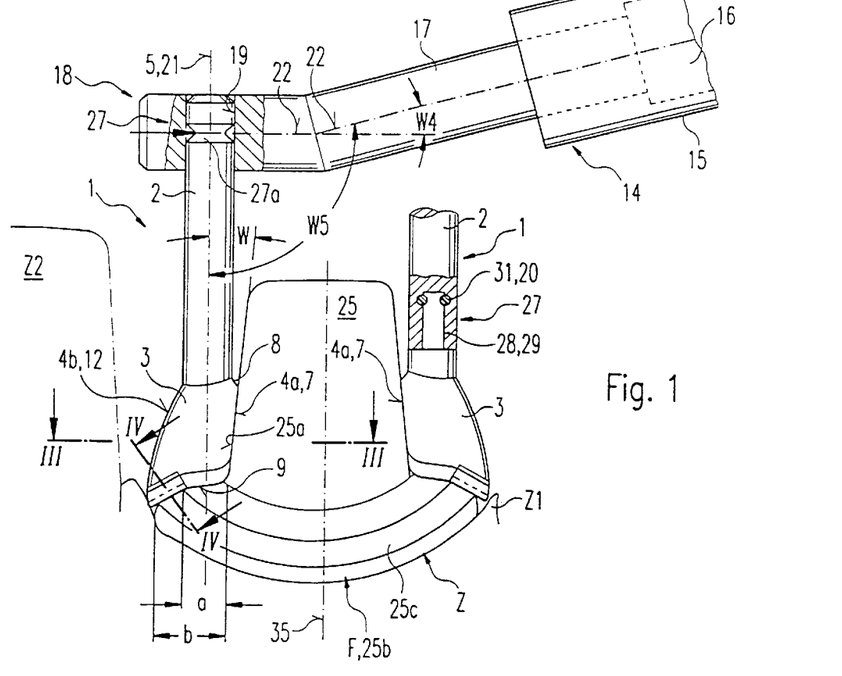
FIG. 1 two tools according to the invention of different design in side view with an associated handpiece and a tooth to be prepared with the respective tool.
Figure 2:
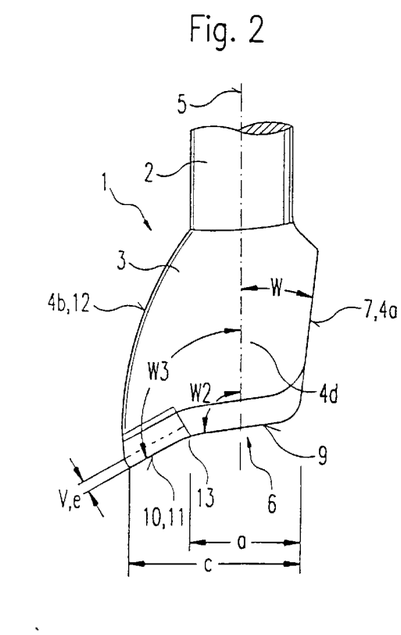
FIG. 2 the tool on the left in FIG. 1, in a somewhat larger representation.

The rear broad lateral face 12 may—seen in the side view according to FIGS. 1 and 2—be convex or straight, intersecting the chamfered processing face 11 at an acute angle. This apex edge is preferably broken or rounded.

The width a of the front-face section 9 amounts to about 0.4 to 0.6 mm, preferably about 0.5 mm, and corresponds approximately to one half of a conventional wall thickness b of a crown of about 0.8 to 1.2 mm. The width c of the front side 6 is the same or somewhat greater than the wall thickness b. The width d of the processing section 3 extending transverse thereto is approximately the same as or gr eater than the cross-sectional dimension of the circular tool shank 2 and amounts to about 2 mm to 2.5 or up to 3 mm, preferably about 2.2 mm.

The chamfered processing face 11 is studded with a plurality of cutting edges which, given an oscillating movement proceeding parallel to the apex line 13 between the chamfered processing face 11 and the front-face section 9, are suitable to remove material from the tooth Z by machining. In particular when the amplitudes of an oscillating movement are relatively small, the amplitudes may also be directed transverse to the apex line 13 or in different directions—ie, three-dimensionally. suitable for an abrasive working face 10 are a plurality of hard grains which are preferably fixed closely alongside one another on the chamfered processing face 11. To this end the chamfered processing face 11 may be diamond-coated in grainy form in a manner known as such.

Since the abrasive grains on the chamfered processing face 11 form a layer having a certain thickness which at its margin bordering the front-face section 9 forms a small step in the front side 6, it is advantageous either to make the working face 10 deeper in stepped manner by a thickness e corresponding to the thickness of the grains or to cause the grains in the region of the apex line 13 to taper towards the front-face section 9, as a result of which a step at the margin of the abrasive coating is prevented.

In the course of the manufacture of the tool 1 the depression V produced beforehand is filled out with an abrasive layer.

For the retention and guidance of the tool 1 and also for the drive thereof, the handpiece 14 is provided which comprises an elongated round gripping sleeve 15 in the form of a casing in which a vibration generator 16, operated electrically or pneumatically for example, is arranged which transmits its vibrational energy to a handpiece shank 17 supported in the handpiece 14 and protruding beyond its front end, in the front end region of which an attachment device 18 with a plug-in hole 19 for the tool shank 2 is disposed, the centre axis 21 of which extends transverse to, in particular approximately at a right angle to, the centre axis 22 of the handpiece shank 17, so that the tool 5 juts out laterally from the handpiece shank 17. A releasable securing element, a screw for example, is indicated in FIG. 1 by an arrow.

Taking the confined spatial conditions in the oral cavity of a patient into account it is advantageous if the front end region of the handpiece shank 17 is somewhat bent or angled towards the side facing away from the tool 1, preferably by an angle W4 of about 5 to 15°, in particular about 100, so that the centre axis 5 of the tool 1 includes with the centre axis of the handpiece 14 an obtuse angle W5 of about 1000.

For the preparation of the tooth Z indicated in FIG. 1, said tooth is prepared on its circumferential surface by machining preferably with a rotating processing tool so as to form a tooth stump 25, the circumferential surface of which is designated by 25a and the stepped face of which is designated by 25b. The angle included between the two last-named faces corresponds roughly to the angle W2 between the broad lateral face 7 and the front-face section 9. With a view to working the chamfered face 25c in by machining, the tool 1 is inserted with the handpiece 14 into the free space F pertaining to the preparation for the crown in such a way that the broad lateral face 7 abuts the circumferential surface 25a, and then after activation of the vibration generator 16 and abutment of the chamfered processing face 11 on the outer margin of the stepped face 25b the tool 1 is moved in the peripheral direction of the tooth stump 25, whereby the chamfered processing face 11 or working face 10 removes the marginal region of the stepped face 25b by machining and works in the chamfered face 25c on the tooth Z. In the course of the movement in the peripheral direction the tool 1 receives good guidance by virtue of the abutment of the broad lateral face 7 on the circumferential surface 25a and of the front-face section 9 on the stepped face 25b, which are consequently guide faces. However, within the scope of the invention good guidance is also already guaranteed when only the broad lateral face 7 abuts the circumferential surface 25a. Within the scope of the invention it is therefore possible for the abrasive working face 10 to extend not only in the region of the chamfered processing face 11 but also at least over a part of the front-face section 9 or as far as the base region of the broad lateral face 7. With such a design the tool 1 is also suitable to process the stepped face 25b by machining and consequently to achieve a well-fitting shape also on the stepped face 25b.

Figure 3:
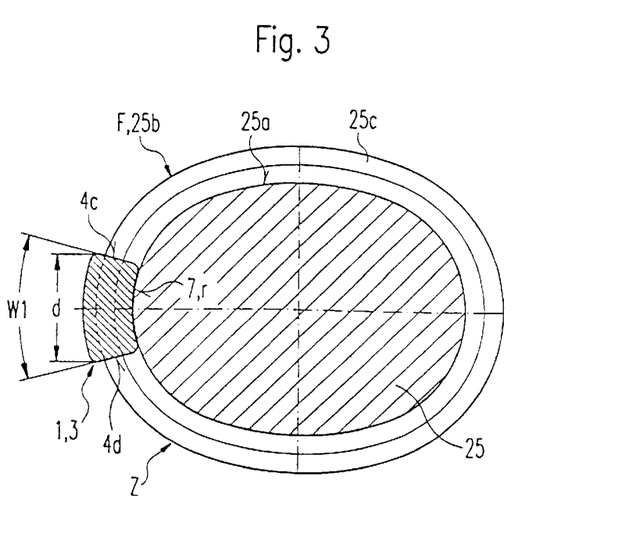
FIG. 3 the section III—III in FIG. 1.

As can best be discerned from FIG. 3, the tool 1 should be rotated about its centre axis 5 in the course of its advance in the peripheral direction of the tooth Z, in order that the abutment of the broad lateral face 7 on the circumferential surface 25a remains guaranteed. This is associated with a considerable ergonomic effort, since a rotation of the tool 1 about its centre axis 5 is only possible to a limited extent, particularly when the cramped spatial conditions in the oral cavity are taken into account. Handling is significantly alleviated when, corresponding to the design according to the right side of FIG. 1, the processing section 3 is supported with respect to the handpiece 2 so as to be rotatable about the centre axis 5. With such a design an automatic rotary adjustment of the processing section 3 takes place in such a way that its broad lateral face 7 always abuts the circumferential surface 25a and in the process of advancing the tool 1 in the peripheral direction the processing section 3 is rotated automatically as a result of the abutment pressure on the circumferential surface 25a. With the design according to FIG. 1 such a rotary joint 27 is disposed either between the processing section 3 and the tool shank 2 or in the region of the tool shank 2. The rotary joint 27 may be constituted by a circular articular tenon 28 and an articular hole 29 receiving it with slight clearance which in the mated position are secured against being pulled apart axially by means of an interlocking device 20, for example by means of an elastically engageable and releasable securing ring 31 which is seated in an annular groove in the tenon 28 or in the articular hole 29 and is capable of elastically engaging a corresponding mating groove on the respective other part. Instead of a securing ring, a securing tenon that is capable of radially inward and outward spring deflection may also be provided which at its free end exhibits a constructional bevel or is rounded in the form of a sphere. With the design according to FIG. 1 the articular tenon 28 is disposed on the processing section 3 and the articular hole 29 is disposed in the tool shank 2.

However, the rotary joint 27 may also be formed by the tool 1 being rotatably supported in a rotary joint 27 in the handpiece 14 or in the handpiece shank 17. It is possible to construct such a rotary joint 27 by the tool shank 2 being supported by at least one bearing, in the seating hole 19 for example, so as to be rotatable about the centre axis 5 but being axially fixed, for example with the screw (arrow) which is set into an annular groove 27a in the tool shank 2 or with an interlocking device (not represented).

If a rotary joint 27 is present, the tool 1 can be held during its advance in the peripheral direction of the tooth stump 25 with its broad side 7 constantly in abutment with the circumferential surface 25a, whereby the processing section 3 or the tool 1 overall constantly follows the circular contour of the circumferential surface 25a and is thereby rotated. In this connection the handpiece 14 may remain in its normal position projecting into the oral cavity of the patient. The broad abutment face or lateral face 7 is preferably rounded in the shape of a cylinder or circular segment so as to conform to the circumferential surface 25a, as a result of which the abutment is improved and stabilised. The radius of curvature r may amount to about 5 to 10 mm. The rear broad lateral face 12 may also be correspondingly rounded.

Figures 4, 5, 6, 7:
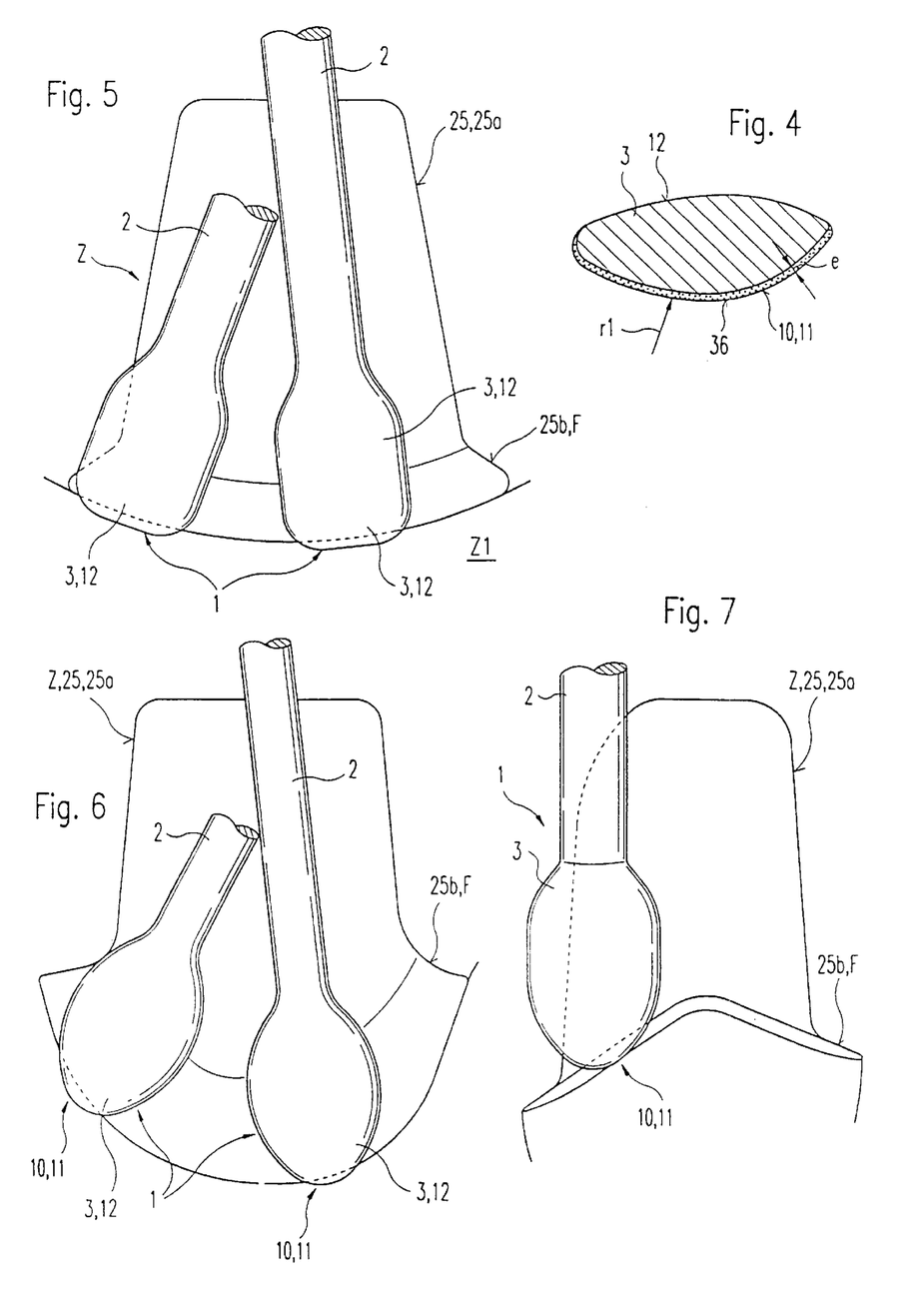
FIG. 4 the partial section IV—IV in FIG. 1.
FIG. 5 a prepared tooth stump viewed from one side with a tool in different working positions.
FIG. 6 a prepared tooth stump viewed from the side with a modified tool in different working positions.
FIG. 7 a prepared tooth stump viewed from the interdental region with a tool located in working position.

With respect to the centre axis 35 of the tooth Z the stepped face 25b does not extend in rotationally symmetrical manner but in the form of a curve so as to conform to the gum Z1 in the lateral region of the tooth Z and in the approximal region, as FIG. 1 and FIGS. 5 to 7 show. The front side 6—ie, the front-face section 9 and the chamfered processing face 11 or working face 10—are therefore, viewed in the oblique section IV—IV in FIG. 1, formed in convex manner, in particular are rounded, the rounding being preferably adapted to the maximal curvature of the stepped face 25b according to FIG. 1, so that the shape of the curve of the stepped face 25b according to FIG. 1 can be worked out preferably in the normal position of the tool with respect to the centre axis 35. However, the convex shape designated by 36 may also be constructed so as to be somewhat flatter than the curvature of the contour of the curve, since the tool 1 is also able to perform machining operations in somewhat oblique working positions, as represented on the left side of FIG. 5 by way of example. With a shape that is rounded according to FIG. 4 the radius r1 amounts to about 0.4 to 5, in particular 3 mm. In this connection the processing section 3, with direction of view towards its rear broad lateral face 12, may be shaped in the sense of a spatula extending parallel or in the sense of a spatula that is convergent towards its free end, the corners at the free end being rounded (see FIG. 5) or the convergently tapering end being rounded (FIG. 6). The design according to FIG. 5 is suitable for a slight concave curvature of the curved shape of the gum Z1, whereas the end shape according to FIG. 6 with angular flanks or the end shape that is convergent in rounded manner is suitable for strong concave curvatures. This applies also to concave curvatures of the gum Z1 according to FIG. 7.

Figure 8:
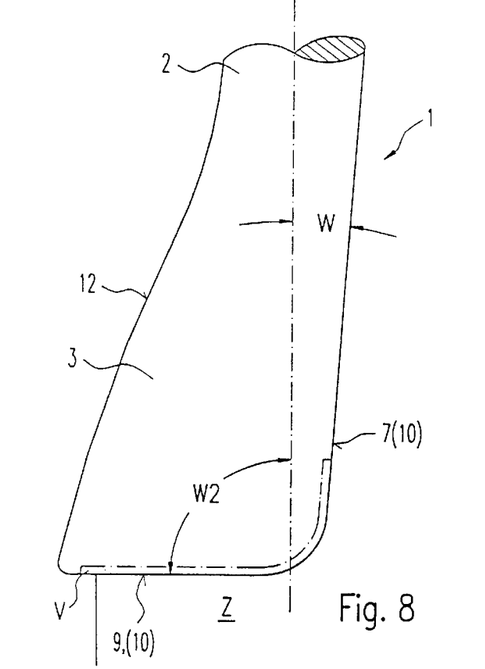
FIG. 8 a tool comprising a further embodiment of the invention.
Figure 9:
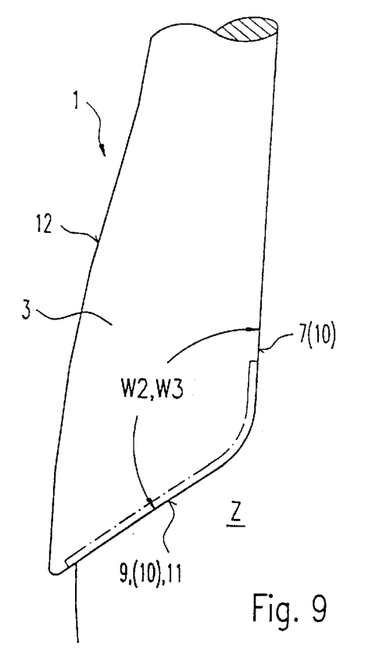
FIG. 9 a tool comprising a still further embodiment of the invention.

As FIGS. 8 and 9 show, the front-face section 9 and the chamfered processing face 11 may also extend in a straight line, whereby the angles W2 and W3 included respectively between them and the centre axis 5 of the tool 1 may amount to about 90° to 135°. In this connection the abrasive working face 10 corresponding to the design according to FIG. 2 may extend only as far as the front-face section 9 or alternatively over a partial region or the entire region of the front-face section 9 or alternatively as far as the associated end region of the broad lateral face 7. In these designs the depression may extend a corresponding distance in the direction of the broad lateral face 7, it being possible for it to extend beyond a facing part of the broad lateral face 7, as is shown. On the rear it is advantageous to cause the depression V to terminate a short distance before the rear broad lateral face 12. As a result, there is no longer a problematic sharp edge at the associated corner of the processing section 3, which would be problematic with regard to possibilities of injury.

Figure 10:
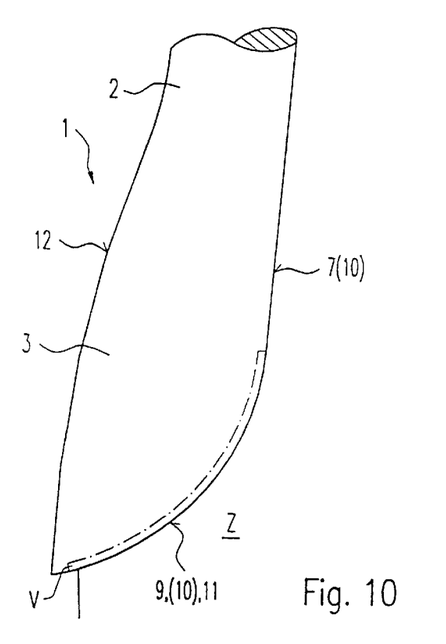
FIG. 10 in each case, a processing section of a tool in modified design in side view.

The embodiment example according to FIG. 10 differs from the two embodiment examples described above according to FIGS. 8 and 9 in that the step of the processing section 3 which is formed by the front-face section 9 and the chamfered processing face 11 is substantially continuously rounded, preferably in the sense of a uniform curvature, seen in the side view according to FIG. 10. With such a processing section 3 a rounded stepped face 25b in the sense of a fillet is generated. Also with this design the depression V may extend only in the exterior free end region of the fillet or alternatively over a partial region under the entire region of the front-face section 9 or alternatively over a facing part of the broad lateral face 7. In this connection the entire front face 6 or its outer part may be an abrasive working face 10.

Within the scope of the invention it is also possible for the abrasive working face 10 to extend over the entire region of the broad lateral face 7, so that the circumferential surface 25a can also be processed abrasively. In this connection it is furthermore possible for the broad lateral face 7 to extend over the entire height of the tooth stump 25. With respect to its support and guidance and its abrasive action the functional region B of the processing head 3 consequently extends over a part of the lateral face 7 or over the entire lateral face 7 and over a part of the front face 6 or over the entire front face 6. With all designs it is possible for a fine preparation of the free space F for the crown to be achieved partially or totally with the tool 1 according to the invention so as to conform to requirements with a high degree of precision.

The remaining faces of the processing section 3, for example the lateral faces 4c, 4d outside the convex shape 36 and in particular the rear lateral face 12, are of smooth construction. By virtue of this, damage to the adjacent tooth Z2 in the case of a position of the tool 1 in the approximal region is avoided.

For the tool 1 there is a risk that when the tool 1 is prevented from executing an oscillating movement it can be overloaded and damaged by reason of an impulse effect resulting from the oscillating movement. With all designs of the tool 1 it is therefore advantageous to provide a damping means 41 in the region of the tool shank 2.

Figure 11:
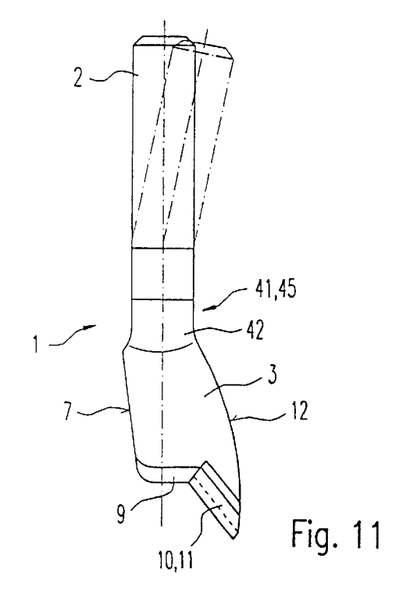
FIG. 11 a tool according to the invention in modified design in side view.

With the design according to FIG. 11 the damping means 41 is located in the region of the tool shank 2, preferably close to or on the processing section 3 or in the transitional region between the tool shank 2 and the processing section 3.

The damping means 41 damps the loading peaks resulting from the oscillating drive and acting on the tool 1, as a result of which the tool is protected against overloads and the risk of damage to or breakage of the tool 1 is avoided or significantly reduced. In this connection the damping means 41 may be effective with respect to forces or impulses directed laterally and/or axially. The damping means 41 enables a relative movement between the sections of the tool 1 between which it is disposed, as a result of which the processing section 3 is kept supple by reason of the flexibility of the damping means 41. Although the damping means 41 transmits the motive force unchanged, the force is transmitted in yielding manner, so that when the tool 1 is prevented from executing its oscillating movement the motive-force peaks are attenuated. This is the case when the amplitudes of the oscillating movement are directed transverse to the working face 10.

With the design according to FIG. 10 the damping element 41 is constituted by an intermediate member 42 made of elastically deformable material, for example plastic or rubber, which is disposed between two tool-shank parts or between the tool shank 2 and the processing section 3 and is firmly connected to these parts, for example by adhesion. Such a damping element 41 is also effective in the peripheral direction.

Within the scope of the invention it is also possible to form the damping element 41 by means of another spring, for example a compression spring with coils or by means of a gas spring, instead of by means of an elastically deformable disc.

The damping means 41 consequently enables both an axial relative movement of the processing section 3 and/or a flexure, the elasticity of the damping means 41 being so great that a minimal compressive force or a minimal flexural moment that is required for the abrasive processing is not fallen short of. By reason of the flexibility in the region of the damping means 41 a universally effective joint 45 is created that enables a lateral flexure of the processing section 3 relative to the tool shank 2, as FIG. 11 indicates. Even in the case of such a flexure the aforementioned minimal torque is not fallen short of, so that the requisite pressure force for the abrasive processing can be transmitted despite flexure. The joint 45 consequently constitutes an oscillating joint in which the processing section 3 is centred by reason of the elastic flexibility.

By reason of the flexibility, the handling during preparation is alleviated, since the processing section 3 can remain in its position in close contact with the tooth stump 25 and guided thereon, although the tool shank 2 is capable of bending outwards in the course of handling.

Figure 12:
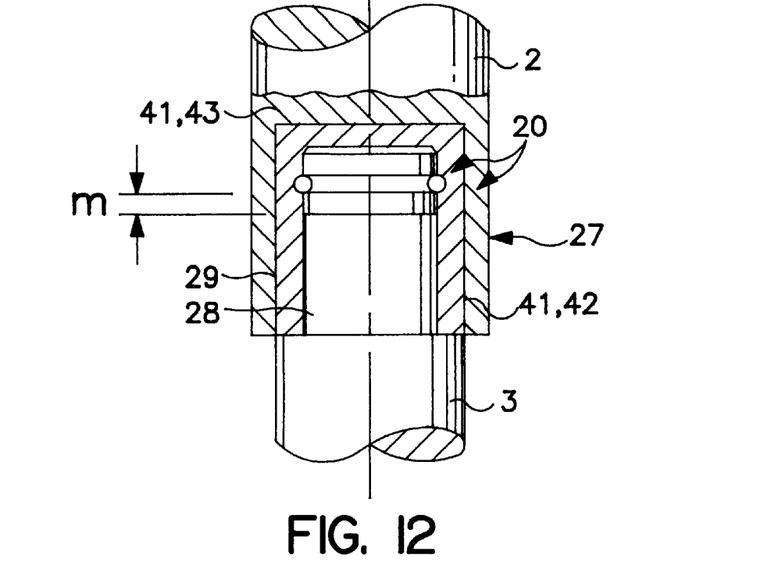
FIG. 12 an embodiment example according to FIG. 11 in axial section.

With the design according to FIG. 12, in which like or comparable parts are provided with like reference symbols, the damping means 41 is integrated into the rotary joint 27. In this case the damping means 41 may also be constructed in such a way that it is capable of damping lateral and/or axial impulses or loading forces and at the same time also permits a lateral bending or buckling movement of the processing section 3. An essential part of the damping means 41 is a sleeve 42 and/or disc 43, each made of elastic material such as, for example, plastic or rubber. The sleeve 42 is disposed between the circumferential surface of the articular tenon 28 and the circumferential surface of the articular hole 29, whereby it may be secured firmly on the articular tenon 28 or firmly against the wall of the articular hole 29, for example it may be fastened with adhesive. The disc 43 is disposed between the articular tenon 28 and the bottom of the articular hole 29, whereby the disc 43 may also be secured on the front side of the articular tenon 28 or on the basal surface of the articular hole 29, for example fastened with adhesive. In the case where the sleeve 42 is present, the damping means 41 is capable of damping lateral loading forces or impulses, whereby the processing section 3 is capable of backing away laterally. In the case where a disc 43 is present, the damping means 41 is capable of damping axial loading forces or impulses, whereby the processing section 3 is capable of backing away axially.

If the sleeve 42 is part of the articular tenon 28, the interlocking device 20 is disposed in the region of the wall of the articular hole 29 and in the region of the outer circumferential surface of the sleeve 42. If the sleeve 42 is secured in the articular hole 29, the interlocking device 20 is disposed in the region of the inner circumferential surface of the sleeve 42 and in the region of the circumferential surface of the articular tenon 28.

If the disc 43 is present, the interlocking device 20 should be constructed in such a way that it permits the possible axial contracting and stretching movements of the tool 1. With the present design this is achieved in that the inner recess or outer recess for the interlocking element is greater by a measurement m than the associated cross-sectional measurement of the interlocking element, so that a relative displacement is possible between the two parts that are capable of interlocking.

Preferably both a sleeve 42 and a disc 43 are present, the damping means 41 preferably being constituted by a cap, as FIG. 12 shows, which may be firmly disposed in the articular hole 29 or on the articular tenon 28.

Figure 13:
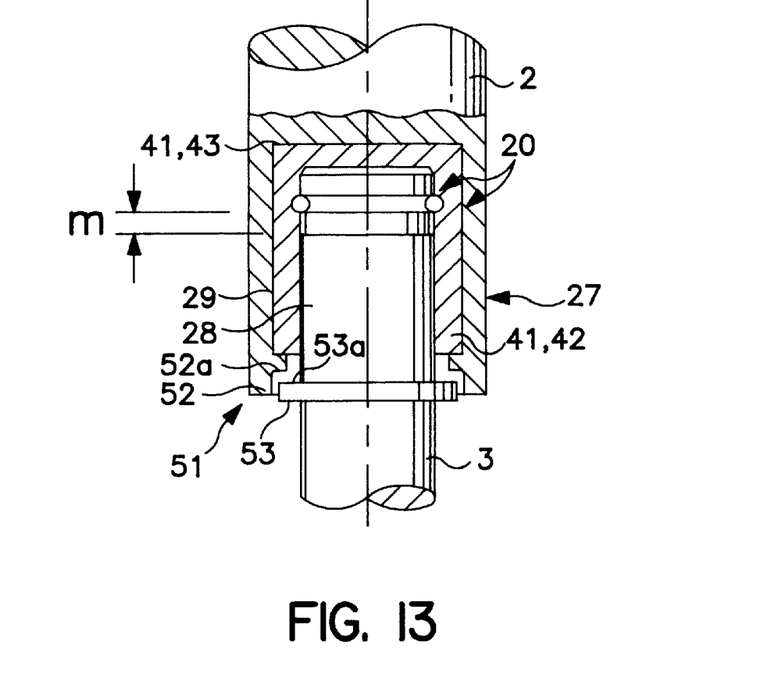
FIG. 13 the embodiment example according to FIG. 12 in a further modified design.

With the design according to FIG. 13 a locking device 51 is assigned to the rotary joint 27, said locking device nullifying the free rotary capacity if the lateral loading on the tool 1 exceeds a predetermined force. This design is particularly advantageous in the case of a crown preparation. If the tool 1 is not to back away as a result of rotation in the course of a preparation, then the rotary joint 27 can be made rigid by activating the locking device 51, so that the processing section 3 cannot back away and is able to perform machining operations in the particular rotary position. This is achieved by virtue of the fact that, in the region of the rotary joint 27 at a radial distance f around the processing section 3, a locking ring 52 is disposed on the tool shank 2 or tool-shank part, here at the margin of the articular hole 29, which in the event of a lateral movement or swivelling of the processing section 3 comes into engagement in non-positive manner with an opposite, second locking ring 53 on the processing section 3 by reason of friction or in positive manner by reason of an engagement with the tooth and thereby prevents the processing section 3 from rotating. The teeth, which are not represented, preferably extend parallel to the centre axis 5, so that given the existence also of an axially effective damping means, here the disc 43 or the cap, the processing section 3 is able to execute an axial movement while it is in engagement with the tooth.

If, for example, the processing section 3 is to be employed for a definite purpose and is to be effective by force at a particular processing site on the tooth, then during processing the lateral pressure on the processing section 3 is increased so intensely that the locking rings 51, 52, which are preferably moulded on in one piece, come into engagement and nullify the rotary capacity of the processing section 3. After a diminution of the lateral loading the processing section 3 returns automatically, by reason of the restoring force of the sleeve 42, to its centred position in which it can be used for abrasive processing by utilising its free rotary capacity.

In those cases in which the damping element 41 is only effective axially, two locking rings 52, 53 should be arranged at an axial distance e from one another in such a way that they come into engagement in the event of an axial movement of the processing section 3. With the design according to FIG. 13 two pairs of locking rings 52, 53 and 52a, 53a are of appropriately angular construction so that the pair of rings 52, 53 come into engagement in the event of a lateral movement and the pair of rings 52a, 53a come into engagement in the event of an axial movement.

The interlocking device 20 makes it possible to equip an associated handpiece with a tool 1 or to exchange a tool 1 in easy-to-handle manner and quickly. It is therefore advantageous to provide, in the form of a set, several tools 1 that differ from one another, that are suitable for different preparatory operations and that can be inserted at will. In this connection it is preferably a question of tools 1 that differ with respect to their preparation shape and/or their capacity to remove material. It is advantageous to provide several tools 1 that have coarse and fine—or coarse, medium and fine—abrasive working faces and consequently enable coarse and fine processing operations and that may differ from one another with respect to their size and/or shape.

All embodiments are suitable for short-stroke oscillations transmitted from the oscillation generator to the processing section 3 in the sense of a vibration at a frequency lying preferably in the sonic or ultrasonic range, it being possible for the oscillations or amplitudes to be directed transversely or lengthwise in linear manner or alternatively three-dimensionally. In the case of the present embodiment example the oscillating drive has a frequency of movement of about 4 to 8 kHz, in particular about 6 kHz, resulting in an amplitude of the three-dimensional movements of about 0.05 mm to 0.25 mm or up to 0.5 mm, in particular of about 0.1 mm, in the region of the processing section 3.

What is claimed is:

1. A dental tool for preparing a tooth for a dental crown, said tool comprising:

an elongated tool shank having an elongated center axis;

a processing section connected to one end of said tool shank;

said processing section having a functional region, said functional region having a lateral face which extends longitudinally in substantially the same direction as said center axis, said functional region also having a front face which is located opposite said tool shank and which extends from said lateral face in a direction substantially transverse to said center axis;

said lateral face being smooth and said front face having an abrasive working surface which constitutes a portion of said front face located at a given distance from said lateral face, and a portion of said front face adjacent said lateral face being smooth.

2. A dental tool according to claim 1, wherein said front face extends in a plane which is at an angle of 90° to 135° with respect to said center axis.

3. A dental tool according to claim 1, wherein said front face is shaped in a convex manner as viewed in a direction transverse to said lateral face.

4. A dental tool according to claim 1, wherein said front face is rounded.

5. A dental tool according to claim 4, wherein said front face is rounded as a segment of a cylinder.

6. A dental tool according to claim 1, wherein the smooth portion of said front face extends smoothly into said lateral face.

7. A dental tool according to claim 1, wherein said abrasive working face forms an angle with said center axis which is greater than the angle that said front face forms with said center axis.

8. A dental tool according to claim 1, wherein said lateral face forms no more than an acute angle with said center axis.

9. A dental tool according to claim 1, wherein said lateral face is rounded in a concave manner as viewed in the direction of said center axis.

10. A dental tool according to claim 1 wherein the abrasive working surface of the front face extends at an angle with respect to the lateral face which is greater than the angle between the smooth portion of the front face and the lateral face.

11. A dental tool for preparing a tooth for a dental crown, said tool comprising:

an elongated tool shank having a longitudinal center axis;

a processing section connected to one end of said tool shank;

said processing section having a functional region, said functional region having a lateral face which extends longitudinally in substantially the same direction as said center axis, said functional region also having a front face which is located opposite said tool shank and which extends from said lateral face in a direction substantially transverse to said center axis;

said functional region having an abrasive working face which constitutes a portion of said front face;

said front face being convex as viewed in an oblique section thereof facing away from said center axis; and said lateral face being rounded in a concave manner in a cross-section thereof taken through said center axis.

* * * * *